United States Patent [19]
McPherson et al.

[11] Patent Number: 5,687,739
[45] Date of Patent: Nov. 18, 1997

[54] BIOPSY SPECIMEN CUTTER

[75] Inventors: William E. McPherson, Tampa; John S. TenBarge, Clearwater, both of Fla.

[73] Assignee: Interventional Concepts, Inc., Tampa, Fla.

[21] Appl. No.: 641,349

[22] Filed: Apr. 30, 1996

Related U.S. Application Data

[63] Continuation-in-part of Ser. No. 567,936, Dec. 6, 1995, abandoned.

[51] Int. Cl.$^6$ .................................................. A61B 10/00
[52] U.S. Cl. .................................................. 128/754
[58] Field of Search .......................... 128/749, 751–754; 606/167, 170

[56] References Cited

U.S. PATENT DOCUMENTS

| | | | |
|---|---|---|---|
| 2,541,542 | 2/1951 | Perez et al. | 128/2 |
| 4,461,305 | 7/1984 | Cibley | 128/754 |
| 4,785,826 | 11/1988 | Ward | 128/754 |
| 4,926,877 | 5/1990 | Bookwalter | 128/754 |
| 5,133,360 | 7/1992 | Spears | 128/754 |
| 5,148,813 | 9/1992 | Bucalo | 128/754 |
| 5,251,641 | 10/1993 | Xavier | 128/754 |
| 5,375,608 | 12/1994 | Tiefenbrun et al. | 128/754 |

FOREIGN PATENT DOCUMENTS

| | | | |
|---|---|---|---|
| 198770 | 3/1965 | Sweden | 128/754 |

OTHER PUBLICATIONS

Staren, Edgar E., "Surgical Office–Based Ultrasound of the Breast", The American Surgeon, vol. 61, pp. 619–627, Southeastern Surgical Congress, Atlanta, 1995.

Staren, Edgar E., "Breast Ultrasound for Surgeons", The American Surgeon, vol. 62, pp. 108–112, Southeastern Surgical Congress, Atlanta, 1996.

*Primary Examiner*—Max Hindenburg
*Attorney, Agent, or Firm*—C. Douglas McDonald, Jr. & Associates, P.A.

[57] ABSTRACT

An improved biopsy specimen cutter utilizes a wire loop, attached to a hand-manipulable trigger mechanism, for severing the tissue sample from the host. A removable dilator is insertable into the biopsy specimen cutter for the purpose of positioning the cutter adjacent the tissue to be removed, and after such placement, the dilator is withdrawn, the specimen cutter is advanced into the tissue, the trigger mechanism is retracted causing the loop to sever the tissue, and the specimen cutter and the specimen contained therein are withdrawn.

28 Claims, 8 Drawing Sheets

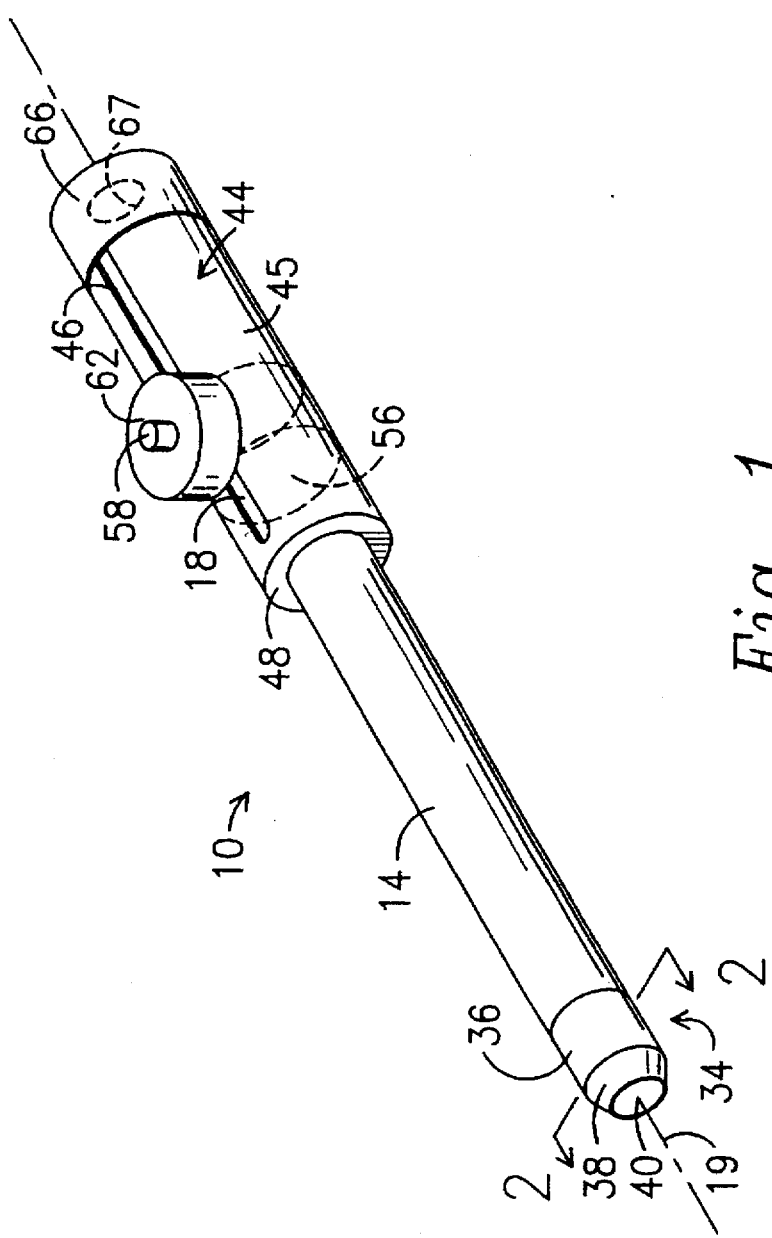
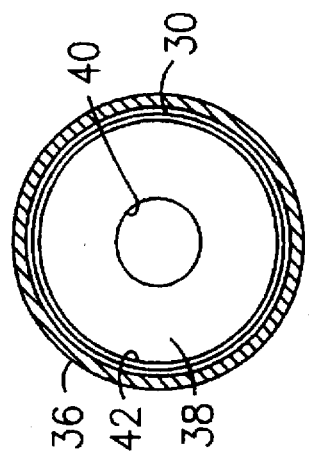

BIOPSY SPECIMEN CUTTER

RELATED APPLICATIONS

This application is a continuation-in-part of application Ser. No. 08/567,936, filed on Dec. 6, 1995, entitled BIOPSY SPECIMEN CUTLER, and filed in the name of William E. McPherson, now abandoned.

BACKGROUND OF THE INVENTION

1. Field of the Invention

The present invention is directed to an improved biopsy specimen cutter of a type primarily intended for use in obtaining a tissue sample. The specimen cutter of this invention is characterized by its simplicity of construction and its structure including the provision of a wire loop as the means for severing the tissue sample from the host.

2. Description of the Prior Art

Prior art patent literature discloses and teaches a wide variety of biopsy instruments. Many such devices comprise elongated hollow tubes having sharpened ends, so that the devices actually bore through tissue to the site from which a tissue specimen is to be collected. Many of these prior art devices also utilize a sharpened dilator, or style, for the purpose of inserting the specimen cutter adjacent the tissue from which the sample is to be taken. The dilator, or style, is removed after initial penetration, and the cutter itself is advanced into the tissue to be collected.

The prior art patents also disclose and teach a variety of means useful for severing the tissue sample from the host. U.S. Pat. No. 2,541,542 to Perez, et al. discloses the use of a thread for this purpose. A moveable, curved blade for cutting the specimen is taught in U.S. Pat. No. 4,926,877 to Bookwalter. U.S. Pat. No. 5,133,360 to Spears discloses the use of a cutting wire which not only severs the tissue sample, but also deforms an end section of that cutter so as to retain the severed specimen therein. U.S. Pat. No. 5,251,641 to Xavier discloses a construction including a rotating inner cannula by which the specimen sample is severed from the host.

Nevertheless, a study of such prior art devices readily leads one to the conclusion that many of the newer devices are relatively complex in their construction, and this increases their cost of construction and, necessarily, their cost to the ultimate end user, the patient. Accordingly, there remains a great need in the art for an improved biopsy specimen cutter that is not only of relatively simple construction but also provides dependable means for efficiently obtaining the desired specimen with a minimum requirement of operator skill and with minimum trauma to the patient.

SUMMARY OF THE INVENTION

This invention is for an improved biopsy specimen cutter of the type primarily intended for use in obtaining a tissue sample. Briefly stated, the specimen cutter of this invention comprises a cutter barrel defined by an elongated hollow tube having a central axis, a first end and a second end. A first wire guide, having a first end and a second end with an aperture formed therethrough, is attached to the first end of the cutter barrel tube. A cutting wire comprising a loop formed on a first end of thereof and at least one wire segment extending from the loop and terminating in a second end of the wire is provided. The loop is disposed on the second end of the first wire guide, with the wire segment and the second end extending longitudinally through the cutter barrel hollow tube and the tube first end. A cutter tip is removably attached to the cutter barrel tube first end substantially enclosing the first wire guide and the wire loop placed thereon between the wire guide and the cutter tip. A trigger housing is attached to the second end of the cutter barrel tube, and the trigger housing is defined by a hollow cylinder having an axially extending sidewall with at least one longitudinal slot formed through the sidewall. The wire second end extends to a position proximal the slot for attachment to a trigger that is mounted inside the trigger housing for axial movement with respect to the trigger housing. The trigger includes a trigger body and a member attached to the trigger body and extending through the slot, with the wire second end being attachable to the trigger member, such that, when attached, pulling the trigger away from the second end of the cutter barrel tube will cause the wire loop to move across the second end of the first wire guide.

In operation, the specimen cutter may be inserted into a host for placement substantially adjacent a tissue to be collected. Then the cutter tip may be urged into the tissue such that at least a portion of the desired tissue sample is positioned within the cutter barrel tube. Once the specimen cutter is positioned properly for removal of the tissue specimen, the trigger is moved rearwardly away from the cutter tip such that the loop moves across the first wire guide second end, thereby severing the portion of the tissue specimen positioned within the cutter barrel, with the tissue sample remaining within the cutter barrel. The tissue specimen may be removed from the patient generally forming a void in the patient's tissue.

BRIEF DESCRIPTION OF THE DRAWINGS

Preferred embodiments of the present invention are illustrated in the accompanying drawings, in which:

FIG. 1 is a perspective view of a preferred embodiment of the improved biopsy specimen cutter of the present invention;

FIG. 2 is a sectional view taken along line 2—2 in the view of FIG. 1;

DETAILED DESCRIPTION

Figure 6:
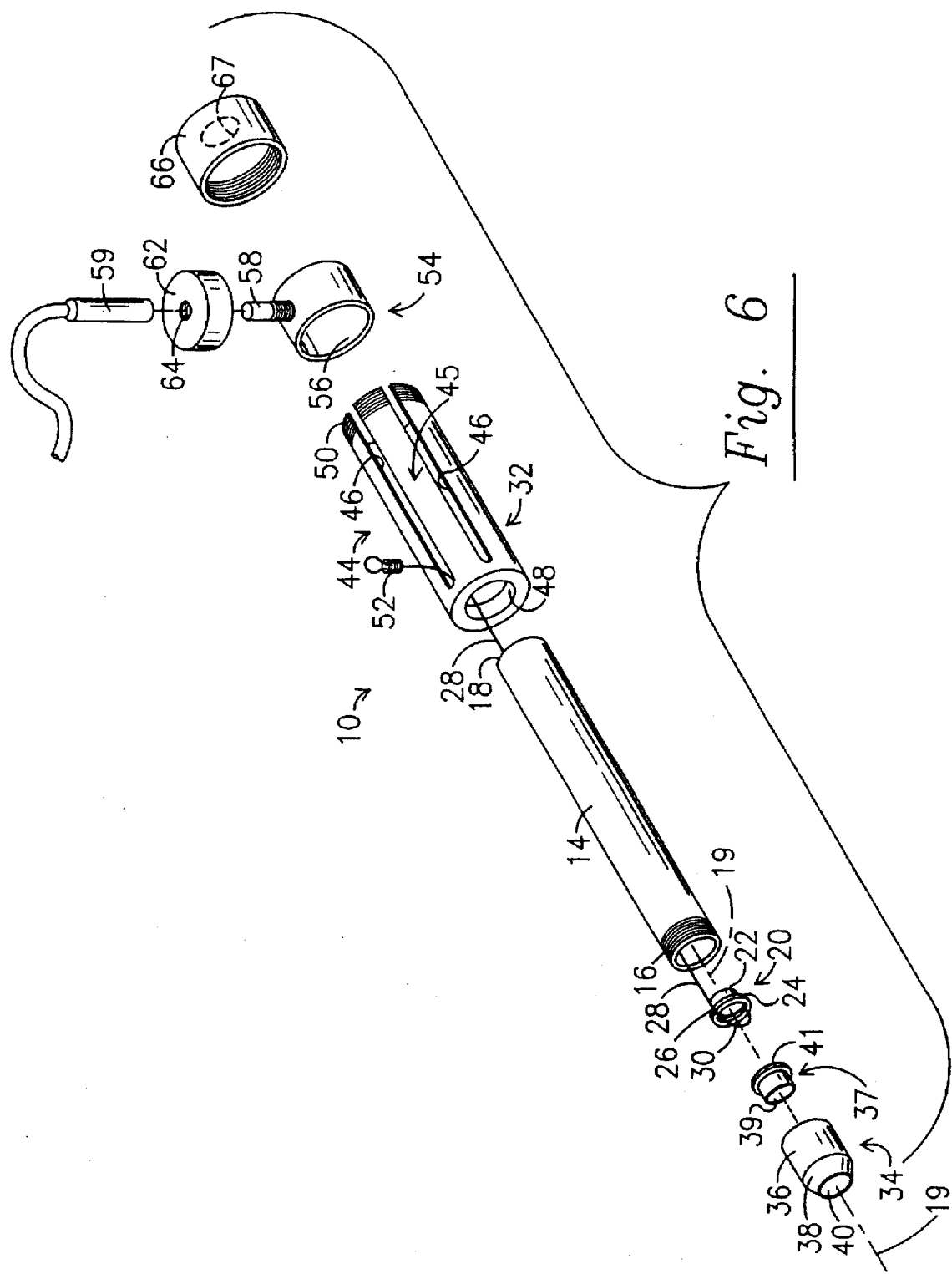
FIG. 6 is an exploded perspective view of an alternative embodiment of the improved biopsy specimen cutter of the present invention.
Figure 7:
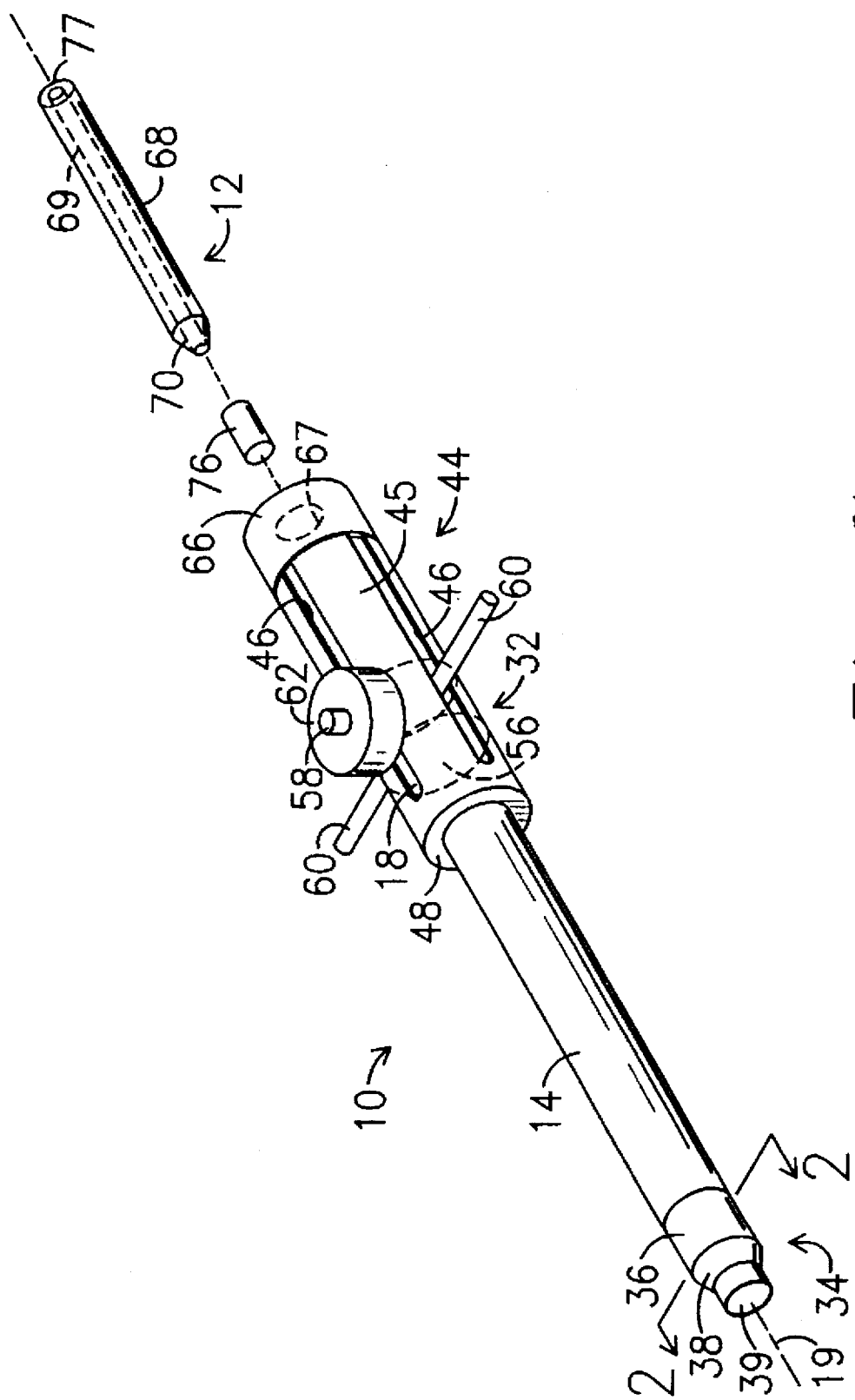
FIG. 7 is a perspective view of the biopsy specimen cutter shown in FIG. 6, shown with the addition of an insertable radio isotope, a dilator and handles.
Figure 8:
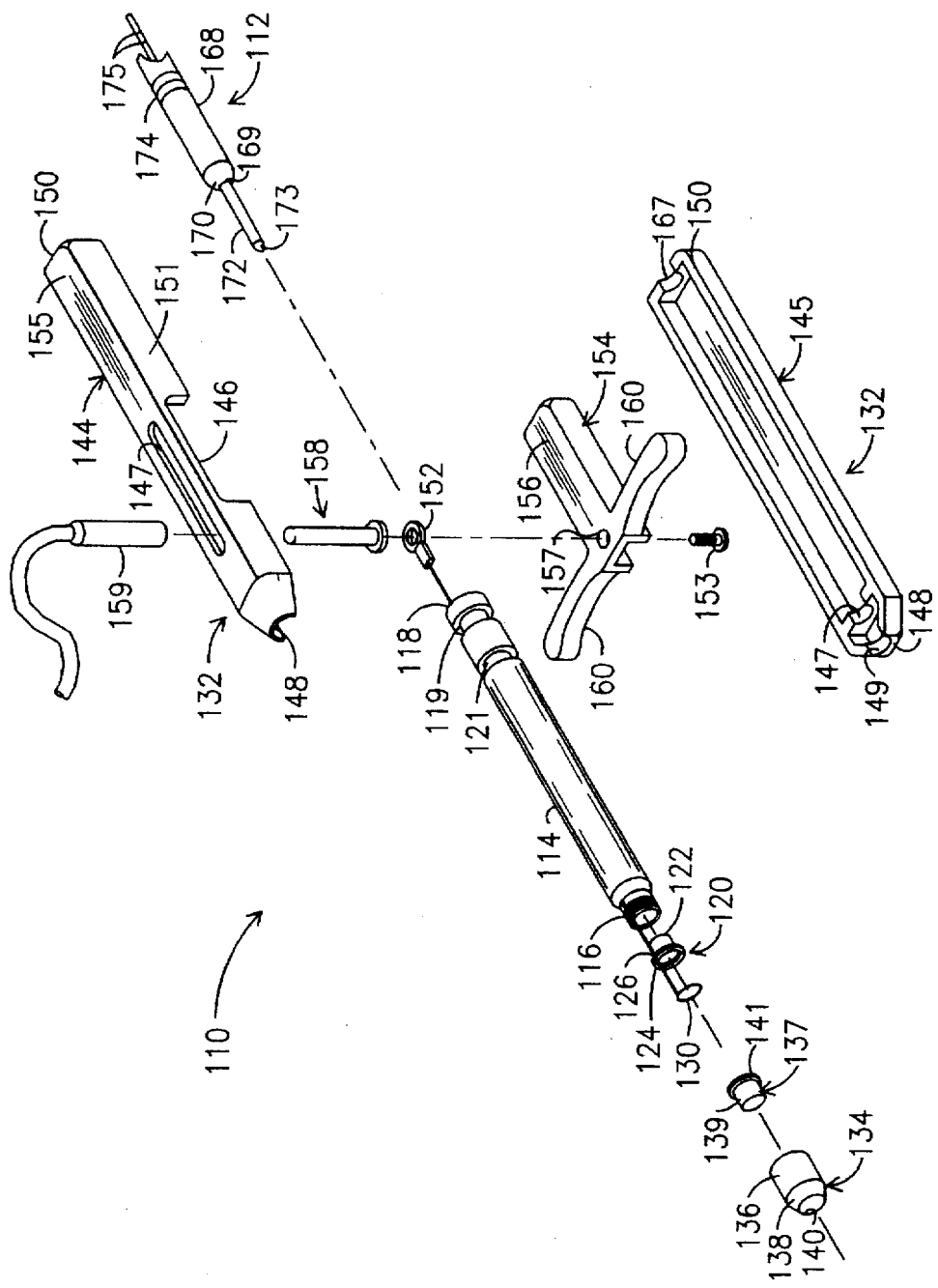
FIG. 8 is an exploded view of an alternative embodiment of the improved biopsy specimen cutter of the present invention, with a fragmentary portion of a dilator.
Figure 9:
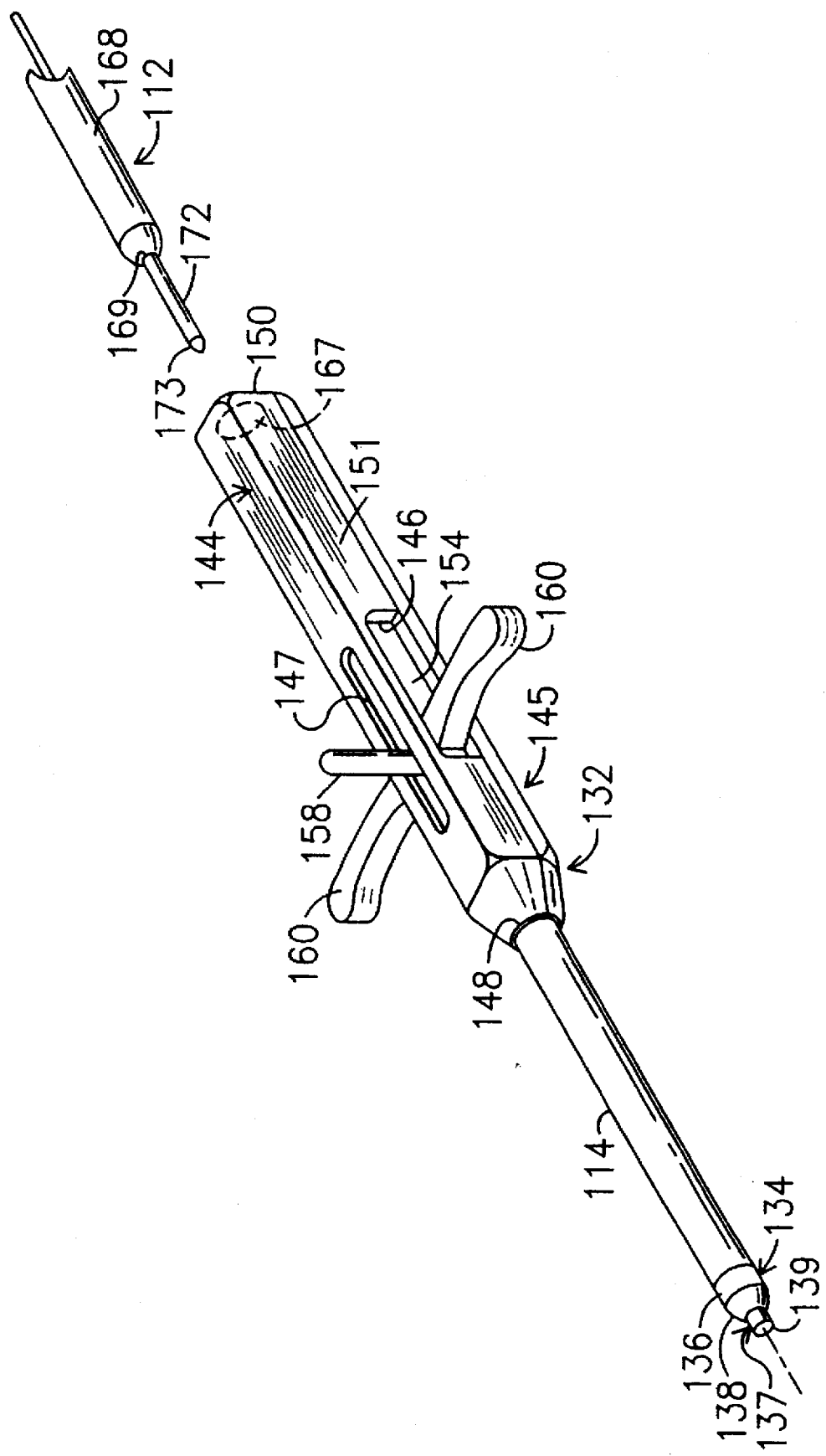
FIG. 9 is a perspective view of the assembled specimen cutter shown in FIG. 8.

The improved biopsy specimen cutter of this invention is generally indicated as in the views of FIGS. 1, 3, 6, 7 and 10 and as 110 in FIGS. 8 and 9. Similar reference characters refer to similar parts throughout the several views of the drawings. While cutter 10 is shown in its assembled, ready-for-use state in the view of FIG. 1, it is to be noted that the exploded view of FIG. 3 also includes a fragmentary representation of a dilator 12, and the purpose and use of dilator 12 will be more fully described hereinafter in connection with the more detailed view of FIG. 4. It is, of course, to be understood that the biopsy specimen cutter is primarily intended for use in obtaining a tissue sample from a host according to well-known procedures.

Figure 3:
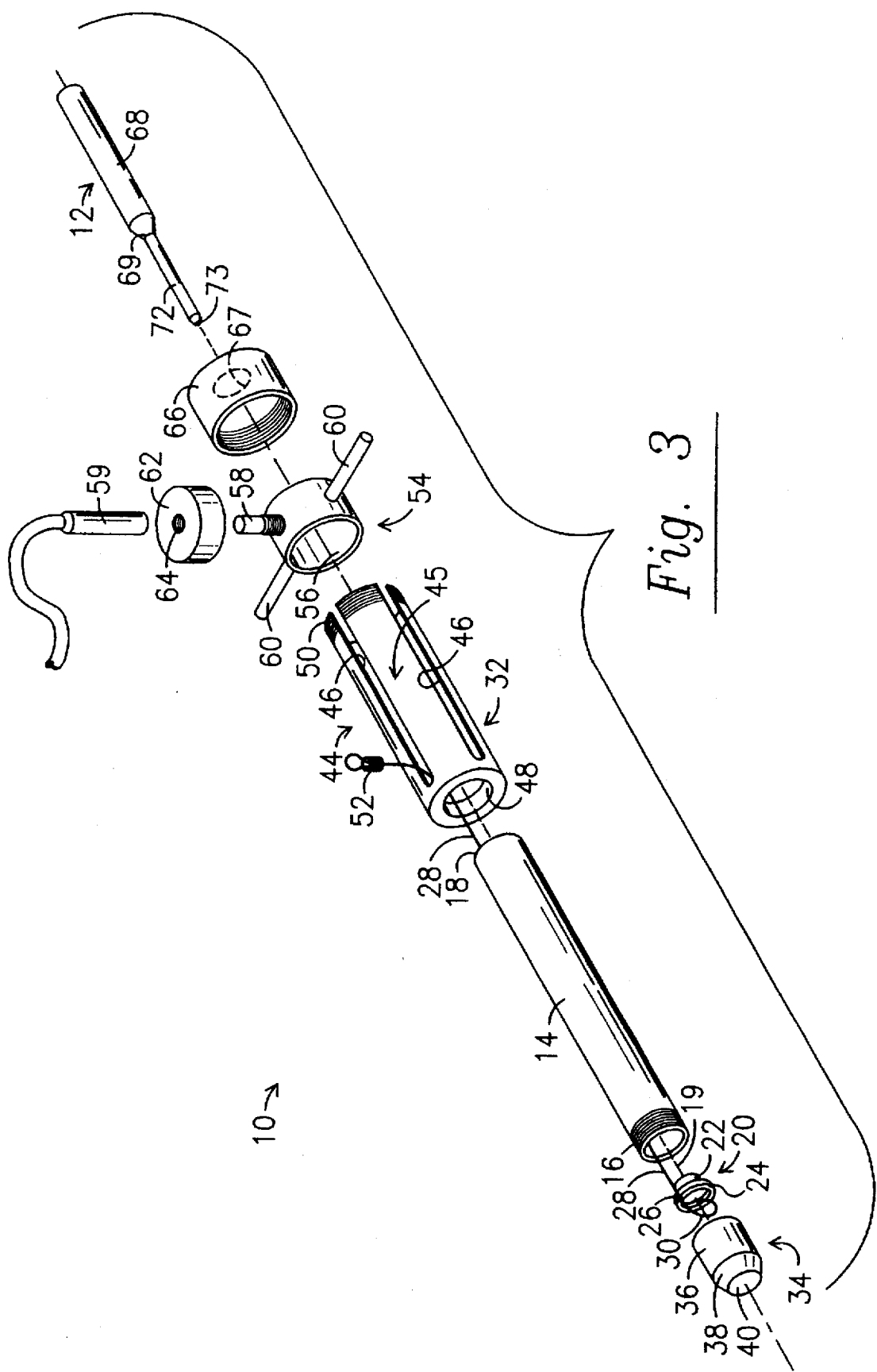
FIG. 3 is an exploded view of the improved biopsy specimen cutter shown in FIG. 1, with the addition of a fragmentary portion of the dilator and handles.

Referring first to the view of FIG. 1, cutter 10 comprises a cutter barrel defined by an elongated tube 14, which may be formed of a generally rigid, lightweight polycarbonate or other synthetic resin material well known in the art. While the tube 14 is illustrated as a generally circular cylinder, other cylindrical shapes may be used with equal facility. As is more clearly seen in the exploded view of FIG. 3, hollow tube 14 preferably includes a threaded first end 16, a second end 18 and a central axis. A first wire guide, generally indicated as 20 in the view of FIG. 3, is in the form of a hollow cylinder generally corresponding to the shape of the cutter barrel first end 16 and may suitably be formed of a substantially rigid, metallic material well known in the art. The first wire guide first end 22 preferably has an outside diameter smaller than the inner diameter of the cutter barrel tube first end 16. As such, the first end 22 of the first wire guide 20 may be attached to the cutter barrel tube first end 16 by insertion of the wire guide first end 22 into the cutter barrel tube first end 16. As illustrated in the view of FIG. 3, the second end 24 of first wire guide 20 has a larger diameter than the diameter of first end 22 that actually abuts first end 16 of hollow tube 14 when the first wire guide is attached thereto. A wire channel 26 is formed on the cylindrical sidewall of the first wire guide 20 proximal the second end 24 thereof, and a wire segment 28 extends from loop 30, which is positioned adjacent to the first wire guide second end 24, through wire channel 26, through tube 14, and into the trigger housing, generally indicated as 32 in the view of FIGS. 1, 3, 6, 7 and 10. Of course, the channel 26 could also be formed proximal the cutter barrel tube first end. Preferably, the wire loop 30 is disposed along the perimeter portion of the surface of the first wire guide second end 24 distal the first wire guide first end 22.

Referring once again to the exploded view of the embodiment of FIG. 3, a cutter tip, generally indicated as 34, is attached to tube first end 16 in surrounding, enclosing relation to first wire guide 20, loop 30, and that portion of wire segment 28 passing through wire channel 26. The cutter tip may be constructed of a generally rigid material, such as surgical steel or a rigid synthetic resin material well known in the art. As clearly seen in the views of FIGS. 1 and 3, cutter tip 34 comprises a hollow cylindrical portion 36 which, in this preferred embodiment, is threaded (not shown) on the interior cylindrical side wall for attachment to cutter barrel first end 16. A frusto-conical portion 38 having a distal end extends opposite the cylindrical portion 36 distal the first end 16, with frusto-conical portion 38 terminating in an end that suitably defines a cutting edge 40.

Referring to the sectional view of FIG. 2, it can be seen that the interior of cutter tip 34 comprises a ledge 42 formed adjacent, or at, the junction of cylindrical portion 36 and frusto-conical portion 38. In this embodiment, loop 30 actually sits between this ledge 42 and the exposed planar surface of second end 24 of first wire guide 20, such that the cutting loop 30 is releasably retained therebetween when cutter tip 34 is attached to cutter barrel tube first end 16.

FIGS. 6 and 7 illustrate an alternative preferred embodiment of the biopsy specimen cutter of the present invention that includes a second wire guide, generally indicated as 37, having first and second ends 39 and 40, respectively, with an aperture formed therethrough. The cutter tip 34 is substantially identical to that described with respect to FIGS. 1–3. The second wire guide 37, which may suitably be formed of a metal, such as conventional surgical steel, is positioned within the cutter tip 34, such that said second wire guide first end 39 extends through the distal end of the frusto-conical portion 38 with the second wire guide second end 41 engaging ledge 42. The first and second wire guides 20 and 37 suitably may be of identical construction with the second wire guide first end 39 sharpened, such as by electrolysis, to define the cutting edge. In addition, the second wire guide second end 41 has an outside diameter greater than the second wire guide first end 39 diameter yet smaller than the inner diameter of the cylindrical portion 36, with the second wire guide 37 being inserted into the cutter tip cylindrical portion 36 such that first end 37 extends through the cutter tip frusto-conical end portion 38. The first wire guide second end 24 is attached to the cutter barrel first end 16 that is positioned generally within the interior of the cylindrical portion 36 of cutter tip 34 adjacent the second wire guide second end 41, with the wire loop 30 interposed between the respective second ends 24 and 39 of the first and second wire guides 20 and 37 respectively. Thus, when the cutter tip 34 is attached to the cutter barrel first end 16, the loop 30 engages the respective perimeter surfaces of the wire guide second ends 24 and 41 such that moving the trigger, generally indicated as 43, away from the cutter barrel tube 14 causes the loop 30 to move across the first wire guide second end 24 and the second wire guide second end 41.

As shown in the several views of the preferred embodiments of the present invention, trigger housing 32 and 132 generally comprises a hollow cylinder 44 having an axially extending sidewall 45 with at least one, and suitably a plurality of longitudinal slots 46 formed through the sidewall 45. Trigger housing 32 may suitably be formed of polycarbonate or other synthetic resin material well known in the art. As shown in the preferred embodiments of FIGS. 3 and 6, hollow cylinder 44 includes one end 48 distal the rear of the apparatus and another end 50 proximal the rear or back end of the apparatus. Distal end 48 is attached to second end 18 of hollow tube 14. It can also be seen that each of the longitudinal slots 46 intersects cylinder proximal end 50 and terminates at a location spaced from distal end 48. It can also be seen that wire second end 52 extends from second end 18 of hollow tube 14 to the interior of hollow cylinder 44 where it may be attached to trigger 43, suitably to member 58.

The trigger 43 is mounted inside trigger housing 32 for axial movement with respect to housing 32. Trigger mechanism 43 comprises a trigger body, suitably a cylinder 56 dimensioned and configured for reciprocal movement generally along the central axis of housing 32. Extending radially from trigger cylinder 56 is a member 58 extending through one of the slots 46. The preferred embodiment also includes at least one, although preferably a pair of, handles 60 extending radially from trigger cylinder 56 and passing through other ones of the longitudinal slots 46. While two handles 60 are shown in the preferred embodiment of FIG. 3, it will be understood that any number of handles or even no handles, as shown in FIG. 1, may suffice for the operation of the specimen cutter 10. Preferably, wire second end 52, which may include a loop, is attached to member 58, suitably a stud, and knob 62 is then removably attached to stud 58 as indicated in the exploded views of FIGS. 3 and 6 and as shown in the view of FIGS. 1 and 7. The attachment of stud knob 62 to stud 58 may be accomplished by providing the exterior of stud 58 with threads and providing corresponding threads on central aperture 64 of knob 62. Thus, for the embodiment of FIGS. 1 and 3, sliding trigger mechanism 43 rearwardly along the longitudinal axis of cylinder 44 will cause loop 30 to move across second end 24 of first wire guide 20, severing any tissue contained within first wire guide 20 and hollow tube 14. Alternatively, for the embodiments of FIGS. 6 and 7 sliding trigger mechanism 43 rearwardly causes the loop 30 to move across the second end 24 of the first wire guide 20 and the second end 41 of the second wire guide 37.

In the embodiment illustrated in FIGS. 1, 3, 6, 7 and 10, it can be seen that proximal end 50 of cylinder 44 is preferably threaded, whereby a correspondingly threaded end cap 66 may be attached to close proximal end 50 and to serve as a stop for trigger mechanism 43. However, it is to be understood that a threaded attachment of end cap 66 to proximal end 50 is not required. Attachment may be by any suitable means, and end cap 66 could even be integrally formed on proximal end 50 such as is illustrated in the preferred embodiment of FIGS. 8 and 9. In the view of FIG. 3 it can also be seen that end cap 66 includes an aperture 67 formed therethrough for insertion of dilator 12 or other articles through the hollow body of specimen cutter 10.

Still another alternative preferred embodiment of the specimen cutter of the present invention is illustrated in FIGS. 8 and 9 in which similar reference numbers, increased by adding 100, refer to similar parts of the specimen cutter shown in FIGS. 6 and 7. The specimen cutter 110 includes a pair of generally opposed first and second wire guides 120 and 137, respectively, of a substantially identical construction to that shown and described with respect to FIGS. 6 and 7; the wire loop 130 is interposed between the respective second ends 124 and 139 of the first and second wire guides 120 and 137, respectively, with the first end 139 of the second wire guide 137 extending through the frusto-conical portion 138 of the cutter tip 134 to define a sharpened cutting edge. A pair of circumferential notches 119 and 121 are formed on the exterior surface of the hollow tube 114 proximal second end 118. The notches 119 and 121 are suitably dimensioned and configured for receiving a pair of corresponding ribs 147 and 149 formed along at least a portion of the interior side wall of the generally cylindrical trigger housing 132, which preferably includes an upper and lower housing, generally indicated as 144 and 145, respectively. The upper trigger housing 144 suitably includes a pair of sidewalls 151 having a longitudinal slot formed intermediate the ends 148 and 150 of housing 132 in which the trigger arms 160 may conveniently extend through for reciprocal movement of the trigger 154 generally along the central axis of the trigger housing 132. The upper housing 144 also includes an upper sidewall portion 155 intermediate sidewalls 151 that also has a longitudinal slot formed therethrough through which trigger member 158, suitably an elongated stud, may extend. The trigger stud 158 and the cutting wire second end 152 are appropriately attached to the trigger 154. As illustrated in FIG. 8, one preferred attachment is forming an aperture 157 through the trigger body 156 and inserting a fastener, such as threaded fastener 153, through aperture 157 into engagement with the trigger body 156, through the loop at the wire second end 152 and attaching it to stud 158, suitably by threading it therein. Of course, other attachment mechanisms may be used with equal facility. With the cutting wire second end 152 suitably attached to the trigger 154 and, preferably, also attached to stud 158, the upper and lower housing 144 and 145, respectively, are appropriately attached together such that ribs 147 and 149 formed proximal distal end 148 of the housing 132 engage at least a portion of notches 119 and 121 to provide a substantially locking attachment, thereby forming the assembled specimen cutter illustrated in FIG. 9. Accordingly, by sliding the trigger 154 rearwardly, suitably by handles 160, the loop 130 will move across the second ends 124 and 141 of the first and second wire guides 120 and 137, respectively, severing tissue that may be positioned within the cutter barrel 114. Trigger 154, cutter barrel 114, cutter tip 134, upper housing 144 and lower housing 145 are suitably formed of a generally rigid material, conveniently by injection molding an appropriate synthetic resin material, which may facilitate the fabrication of the specimen cutter. The end 150 proximal the rear or back of the trigger housing 132 suitably includes an aperture 167 through which an appropriate dilator 168 may be inserted to facilitate positioning the cutting edge 139 of the specimen cutter 110, as discussed below.

In a preferred construction of the specimen cutter 10 and 110, the loop 30 or 130, wire segment 28 or 128 and member 58 or 158 are suitably constructed of an electrically conductive material well known in the art such that an appropriate current, such as from an electric cautery device during electrosurgery, may be applied to member 58 or 158 to facilitate severing the desired tissue but preferably not discolor the excised tissue. In general, less than 200 amperes, suitably 125 amperes, of a high frequency alternating electrical current may be applied to the wire segment or to the trigger member 58 or 158, suitably electronically connected to the cutting wire by connector 59 or 159, for about five to ten seconds during the procedure. In addition, it may be preferable to include a nonconducting ring between the respective wire guides 20 or 120 and 37 or 137 or to coat the respective wire guides with a non-conducting layer to minimize the effects of the electrosurgery on the tissue surrounding the excised tissue.

Figure 4:
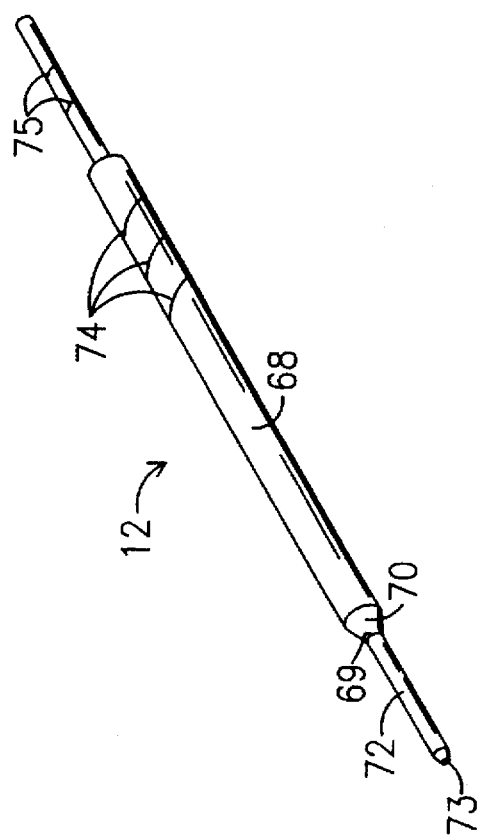
FIG. 4 is a perspective view of the assembled dilator shown in FIG. 3.

Preferred constructions of the elongated dilator 12 are shown in the views of FIGS. 3, 4, 7, 8 and 9. The dilator 12 or 112 is insertable through the biopsy specimen cutter, such that when inserted through the cutter and the first end 70 or 170 may extend beyond the cutter tip 34 or 134 to facilitate generally the positioning of the cutter tip 34 or 134 proximal a tissue sample. Preferably the main body 68 or 168 includes a longitudinal aperture 69 or 169 formed therethrough in which a needle 72 or 172 may be inserted into such that the needle tip 73 or 173 may extend beyond dilator first end 70 or 172 to further facilitate positioning the cutting edge. More particularly, when assembled as shown in FIG. 4 and inserted into specimen cutter 10 or 110, tip 73 or 173 of needle 72 or 172 and distal end 69 or 169 of main body 68 or 168 extend outwardly beyond cutting edge 40, 39 or 139. By referring to body indicia 74 or 174 placed on the outside of main body 68 and to needle indicia 75 or 175 placed on the outside of needle 72 or 172, the user of cutter 10 or 110 can determine the relative placement of the cutter 10 or 110 inside a patient's tissue from which the specimen is to be removed. In addition, indicia may also be placed on the outside of the cutter barrel tube 14 or 114. Once initial placement of cutter 10 has been so determined, needle 72 or 172 and main body 68 or 168 may be retracted so that the cutting edge 40, 39 or 139 may be inserted into the tissue for obtaining the desired specimen.

Another use of the dilator 12 is illustrated in FIG. 7. In this embodiment, the dilator 12, having first and second ends 70 and 77, respectively, is used in combination a quantity of a suitable radio isotope implant or seed, such as iridium-192, cobalt-60 or other isotopes well known in the art for interstitial therapy, suitably brachytherapy. The seed 76 provides radiation therapy to a patient by implanting it within or adjacent the cancerous tumors. Such isotope seeds 76 are commonly used with breast cancer patients either in combination with or in place of a traditional mastectomy. Such isotope seeds 76 are well suited for use with the biopsy specimen cutter 10 of the present invention. After the specimen cutter 10 excises an appropriate tissue sample from a patient forming a void, a quantity of the radio isotope 76 may be inserted into the specimen cutter aperture 69, suitably through the end cap 66, followed by the elongated dilator 12. The dilator 12 may urge the particle through the trigger housing 32, through the cutter barrel 14 and through the cutter tip 34 into the void formed by excising the tissue sample.

Figure 10:
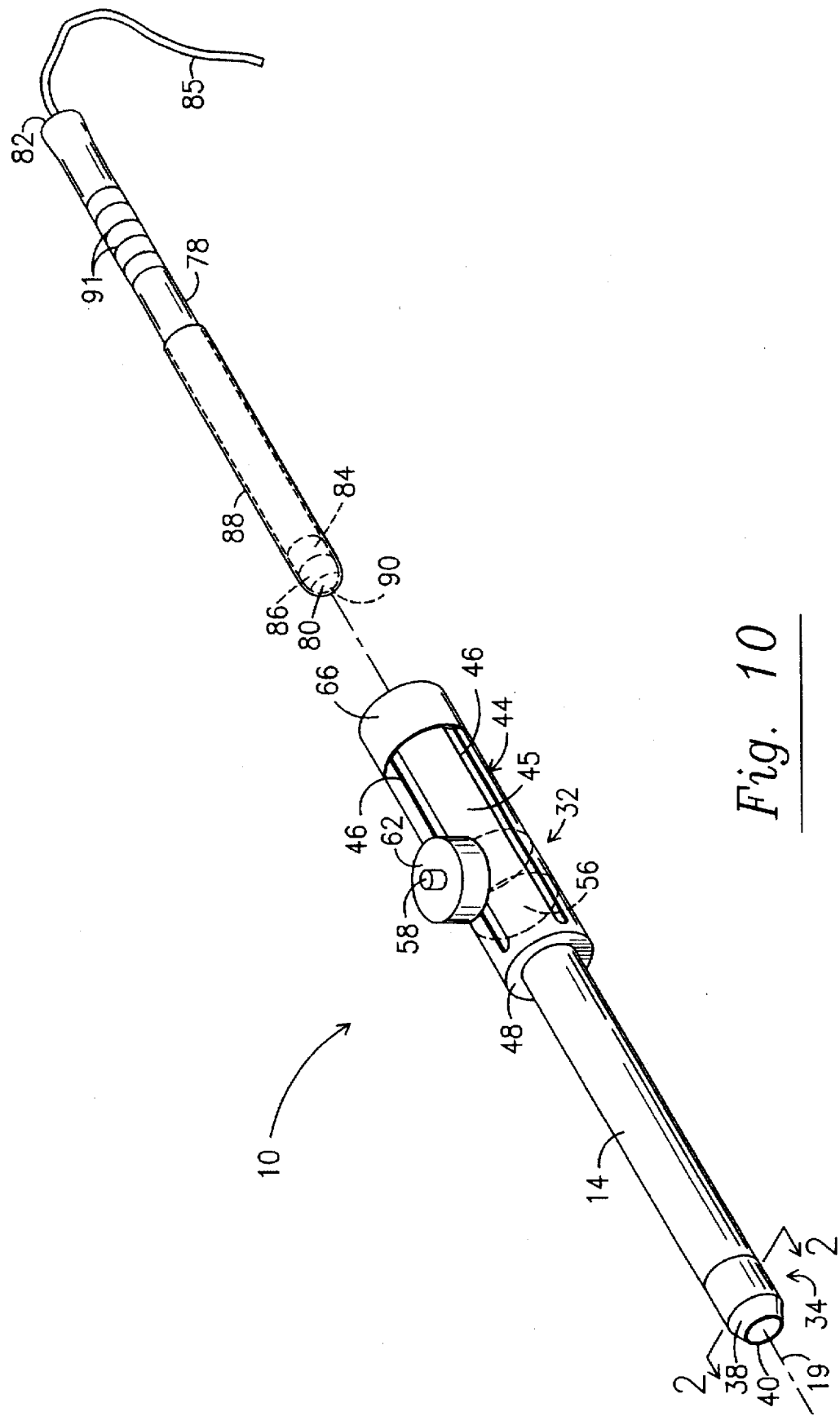
FIG. 10 is a perspective view of the biopsy specimen cutter shown in FIG. 1, with the addition of an ultrasonic probe insertable within the specimen cutter.

Referring to FIG. 10, the apparatus 10 of the present invention may further be enhanced by including an ultrasonic probe 78, which may suitably be used as a dilator, having first and second ends 80 and 82, respectively, with the probe 78 being dimensioned and configured for insertion the axial movement within the biopsy specimen cutter 10 and through the cutter tip 34. The probe 78 illustrated in FIG. 10 is an elongated rod that includes a transducer 84 of an appropriate piezoelectric crystal that is well known in the art of ultrasonography. The transducer 84 includes a sole 86 affixed to the first end 80 of the probe structure 78. Such transducer 84 may either be of mechanical or electronic construction, as is well known in the art, and includes means for generating and receiving ultrasound waves suitably in the frequency range of 4 to 15 MHz, preferably about 7.5 MHz. As is well known in the art, the transducer 84 includes a conventional piezoelectric crystal that converts electrical energy into sound waves and receives the ultrasound echoes, which it converts back to electrical energy suitable for image display. The transducer 84 is coupled, such as by cord 85, to a conventional display for producing a visual image representation according to the ultrasound waves produced and received at transducer 84. As is well known in art, the display means generally includes a suitable data processing unit coupled to the transducer and to the display for converting the electrical signals from the transducer into a visual representation thereof. Depending upon the particular display, a conventional scan converter may also be employed to further convert the acquired data from the transducer to the required format and rate for display at the display means. In operation with the present invention, such ultrasonic probe 78 may be used invasively by insertion within a patient's tissue to facilitate or guide the positioning of the cutter tip 34 at the target tissue of a patient host. This apparatus is particularly well suited for breast cancer patients. For example, the general location of cancer tissue and the initial incision point may be determined from a conventional mammogram. The ultrasonic probe 78 is then inserted through the incision point into the patient's tissue where it acts as a dilator as well as provides an image from which one skilled in the art may ascertain the surrounding tissue composition and the distance between the probe 78 and the tissue to be excised. This information together with suitable indicia or markings 91 on the cutter exterior surface generally provide means for the user to position the cutter tip adjacent the tissue to be excised. Due to the relatively small surface area of such a sole 86 of the transducer, the sole 86 suitably may be convex shaped in order to provide a generally sector-shaped representation of the surrounding tissue at the display.

In order to provide an appropriate interface between the ultrasonic probe 78 and the host tissue, a sheath 88 of a flexible material, suitably a latex rubber or the like, generally surrounds the rod first end and the transducer with a viscous fluid material 90, suitably a conventional ultrasonic gel well known in the art, interposed between the transducer and the sheath 88 to provide the appropriate conducting interface between the transducer and the sheath. Alternatively, the fluids and fatty tissue within the host patient's body may provide an adequate interface such that sheath 88 and gel 90 may not be necessary.

Figure 5:
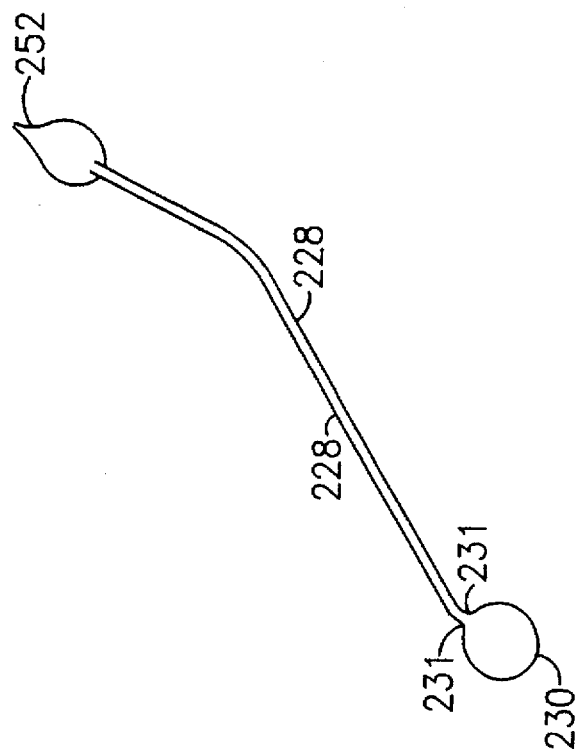
FIG. 5 is a detail view of a second preferred cutting wire for the invention.

Another preferred embodiment for the cutting wire 228 of this invention is shown in the view of FIG. 5. As shown in that figure, the cutting wire comprises a single piece of wire 228 that is doubled back on itself to define a loop 230 between first ends 231 of wire 228 and to define a pair of wire second ends 252. Utilizing this embodiment of the cutting wire and the embodiment of specimen cutter illustrated in FIGS. 1 and 3, loop 230 actually sits between ledge 42 and the exposed planar surface of second end 24 of first wire guide 20 when cutter tip 34 is assembled to first end 16. Alternatively for the embodiments shown in FIG. 6 and 7 or FIGS. 8 and 9, the loop 230 is positioned between the second ends 24 and 41 or 124 and 141 of the respective first and second wire guides 20 and 37 or 120 and 137, respectively. Both segments of wire 228 extend from loop 230 through wire channel 26, through tube 14, into hollow cylinder 44, and out through one of the longitudinal slots 46. Wire second ends 252 may then be attached to stud 58 and be held there by stud knob 62, shown in FIGS. 3 and 6, or be attached to the trigger 154 as shown and described with respect to FIGS. 8 and 9.

Having thus set forth preferred constructions for the biopsy specimen cutter 10, it is to be understood that the scope of the invention is not to be limited to these particular constructions. It is also to be understood that the various parts of cutter 10 may be formed from appropriate materials including, for example, metals and plastics. This is also true for the alternative embodiments of the loops 30 or 130 and wire segments 28 or 128, including wire second ends 52 or 152 as illustrated in FIGS. 3, 5 and 6. While the term "wire" is used to describe these elements, that term is intended to include not only metals, but also plastics, unless specified otherwise.

Furthermore, while the cutter 10, as thus far described and explained, is operable for removing a tissue sample once it has been inserted, the use of dilator 12 is desirable for initial insertion. As shown in the view of FIGS. 3 and 4, dilator 12 comprises a main body 68 with a longitudinal aperture through which a needle 72 may be inserted. For initial insertion of cutter 10, dilator 12 is inserted through aperture 67 so that tip 70 extends outwardly beyond cutting edge 40 of cutter tip 34. The needle 72 may extend through end 70 to define further the placement of the cutter tip 34. Of course, as set forth above, this procedure may further be enhanced by utilizing the ultrasonic probe 78 in place of the conventional dilator 12 to more accurately guide the cutting edge 40 to the desired tissue sample. Thus assembled, the cutter 10 is inserted until cutting edge 40 is substantially adjacent the tissue from which the specimen is to be collected. The dilator 12 is then retracted an appropriate distance, as indicated by main body indicia 74 and needle indicia 75, so that the cutter 10 can be inserted into the tissue from which the specimen is to be collected. According to standard procedures, the entire cutter 10 would then be advanced preferably with a rotating, or twisting motion so that the cutting edge penetrates the tissue from which the specimen is to be collected. This would result in specimen tissue entering cutter tip 34, passing through the central bore of first wire guide 20 into the interior of cutter barrel tube 14. When the user of cutter 10 had determined sufficient penetration into the tissue from which the specimen is to be collected, trigger 43 would be moved rearwardly, suitably by handle 60. For each of the preferred embodiments of the cutting wire illustrated in the figures, as tension is placed on the wire segment 28 or 228, loop 30 or 230 would be pulled through the tissue, resulting in the severing of the specimen inside tube 14. The operator could remove the excised specimen contained therein by pulling rearwardly on handle 60. If necessary, the specimen may be removed from the specimen cutter by the use of forceps, a screw retractor, or other such device well known in the art. Regardless of which embodiment of the cutting wire is used, it should be noted that proper placement of the loop 30 or 230 is best accomplished by disposing the loop 30 or 230 around the main body 68 of the dilator 12 before attaching cutter tip 34 to the first end 16. Then, the second end of the cutting wire 52 or 252 may be pulled rearwardly and attached to the stud 58 such as by knob 62. In this manner, attaching cutter tip 34 to the first end 16 will substantially ensure proper placement of loop 30 or 230 between ledge 42 and the planar surface of the second 24 of the first wire guide 20. Alternatively, for the preferred embodiments illustrated in FIGS. 6 and 7 or FIGS. 8 and 9, the dilator 12 or 112 may be positioned through the first wire guide 20 or 120, the loop 30 or 230 and the second wire guide 41 or 141 before attaching the cutter tip 34 or 134 to the first end 16 or 116 to ensure proper placement of the loop 30 or 230 between the perimeter surface of the respective second ends 24 and 41 or 124 and 141 of the first and second wire guides 20 and 37 or 120 and 137 respectively.

While the foregoing describes in detail preferred embodiments of the apparatus and method of this invention, it is to be understood that such description is illustrative only of the principles of the invention and is not to be considered limitative thereof. Because numerous variations and modifications of the present invention will readily be apparent to those skilled in the art, the scope of this invention is to limited solely by the claims appended hereto.

What is claimed is:

1. An improved biopsy specimen cutter of the type primarily intended for use in obtaining a tissue sample, said cutter comprising:

a cutter barrel comprising an elongated hollow tube having a central axis, a first end and a second end, a first wire guide having a first end and a second end with an aperture formed therethrough, said first wire guide attached to said cutter barrel tube first end;

a cutting wire comprising a loop formed on a first end of said wire and at least one wire segment extending from said loop and terminating in a second end of said wire, said loop being positioned adjacent, to said second end of said first wire guide, and said wire segment and said wire second end extending longitudinally through said cutter barrel hollow tube;

a cutter tip removably attached to said tube first end substantially enclosing said first wire guide;

a trigger housing attached to said second end of said cutter barrel tube, said housing comprising a hollow cylinder having an axially extending sidewall with at least one longitudinal slot formed through said sidewall, said wire second end extending through said one slot; and a trigger mounted inside said housing for axial movement with respect to said housing, said trigger comprising a trigger body and a member attached to said trigger body and extending through said slot, with said wire second end being attachable to said member, such that attaching said wire second end to said member and pulling said trigger away from said cutter barrel tube second end will cause said loop to move across said second end of said first wire guide, whereby the loop movement across the second end cuts the tissue sample.

2. An improved biopsy specimen cutter according to claim 1 wherein said hollow cylinder of said trigger housing further comprises a plurality of said slots with said member extending through one of said slots, and at least one handle extending through another of said slots and attached to said trigger body.

3. An improved biopsy specimen cutter according to claim 1 further comprising an end cap attachable to said housing to block removal of said trigger from said trigger housing.

4. An improved biopsy specimen cutter according to claim 1 wherein said cutter barrel first end has an inner diameter, and said first wire guide is in the form of a generally hollow cylinder generally corresponding in cross-sectional shape to the shape of the cross-section of said cutter barrel tube first end, said first wire guide having a first end with an outside diameter smaller than said inner diameter of said first end of said cutter barrel tube, with said first end of said first wire guide being attachable to said first end of said cutter barrel tube by insertion of said wire guide first end into said cutter barrel tube first end.

5. An improved biopsy specimen cutter according to claim 4 wherein said first wire guide second end has an outside diameter greater than said outside diameter of said first wire guide first end and said cutter barrel tube inner diameter.

6. An improved biopsy specimen cutter according to claim 5 wherein said first wire guide second end further comprises a wire channel formed on the cylindrical sidewall of said first wire guide proximal the second end thereof, such that said wire segment may extend from said loop, through said wire channel, through said hollow tube and to said trigger member.

7. An improved biopsy specimen cutter according to claim 6 wherein said cutting wire loop is disposed on the surface of said first wire guide second end distal said first wire guide first end.

8. An improved biopsy specimen cutter according to claim 4 and further comprising a second wire guide having a first end and a second end with an aperture formed therethrough, said second wire guide first end attached to said cutter tip and defining a cutting edge that extends through said cutter tip, said second wire guide second end positioned adjacent said first wire guide second end with said loop interposed between said second wire guide second end and said first wire guide second end when said cutter tip is attached to said cutter barrel first end, such that pulling said trigger away from said second end of said cutter barrel tube will cause said loop to move across said first wire guide second end and said second wire guide second end.

9. An improved biopsy specimen cutter according to claim 8 wherein said second wire guide second end has an outside diameter greater than said second wire guide first end outside diameter.

10. An improved biopsy specimen cutter according to claim 8 wherein said cutter tip comprises a hollow cylindrical portion having an inner diameter attached to said cutter barrel tube first end, and a hollow, frusto-conical portion having a distal end with the smallest diameter of said frusto-conical portion having an aperture formed therethrough and extending from said cylindrical portion, said second wire guide positioned within said cutter tip such that said second wire guide first end extends through said distal end of said frusto-conical portion.

11. An improved biopsy specimen cutter according to claim 10 wherein said second wire guide first end has an outside diameter smaller than said diameter of said cutter tip frusto-conical aperture, and said second wire guide second end has an outer diameter smaller than said cylindrical portion inner diameter, with said second wire guide attached to said cutter tip by insertion of said second wire guide first end into said cutter tip cylindrical portion.

12. An improved biopsy specimen cutter according to claim 11 wherein said cutter tip has an interior with a ledge formed on the interior thereof generally adjacent the junction of said cylindrical portion and said frusto-conical portion, such that said second wire guide second end engages said ledge, with said loop releasably retained between the respective said second ends of said wire guides when said cutter tip is attached to said cutter barrel tube first end.

13. An improved biopsy specimen cutter according to claim 1 wherein said cutter tip comprises a hollow cylindrical portion attached to said cutter barrel tube first end, and a hollow, frusto-conical portion extending opposite said cylindrical portion, the end of said cutter tip frusto-conical portion defining a cutting edge.

14. An improved biopsy specimen cutter according to claim 13 wherein said cutter tip has an interior with a ledge formed on said interior thereof adjacent the junction of said cylindrical portion and said frusto-conical portion, such that said cutting wire loop is releasably retained between said ledge and said first wire guide second end when said cutter tip is attached to said cutter barrel tube first end.

15. An improved biopsy specimen cutter according to claim 1 wherein said trigger housing further comprises a cylinder distal end and a cylinder proximal end, said trigger housing further comprising a plurality of longitudinal slots formed through said cylinder sidewall, each of said slots intersecting said cylinder proximal end, and each of said slots terminating at a location spaced from said cylinder distal end, said cylinder distal end being attached to said cutter barrel tube second end.

16. An improved biopsy specimen cutter according to claim 1 further comprising an elongated dilator having first and second ends, said dilator being insertable through said biopsy specimen cutter, such that, when inserted through said biopsy specimen cutter, said first end of said dilator extends beyond said cutter tip to facilitate positioning said cutter tip proximal the tissue sample.

17. An improved biopsy specimen cutter according to claim 16 further comprising a quantity of a radio isotope material insertable within said biopsy specimen cutter adjacent said first end of said dilator, such that said dilator may urge said material through said biopsy specimen cutter proximal the tissue sample.

18. An improved biopsy specimen cutter according to claim 16 wherein said dilator comprises a dilator main body having a longitudinal aperture formed there-through, with said biopsy specimen cutter further comprising a needle having a needle tip formed on a distal end thereof, said needle being insertable through said main body of said dilator such that said needle tip extends beyond said cutter tip to facilitate positioning said cutter tip proximal the tissue sample.

19. An improved biopsy specimen cutter according to claim 18 wherein said dilator is retractable from said biopsy specimen cutter when said cutter tip has been positioned adjacent the tissue sample.

20. An improved biopsy specimen cutter according to claim 1 wherein said biopsy specimen cutter further comprises a knob removably attachable to said member, such that said wire second end may be attached to said member by affixing said knob thereto.

21. An improved biopsy specimen cutter according to claim 20 wherein said trigger body is dimensioned and configured for reciprocal movement along a central axis of said housing, said member extending radially from said trigger body through said one slot.

22. An improved biopsy specimen cutter according to claim 1 wherein said cutting wire comprises a loop formed between opposed respective first ends of a pair of wire segments extending from said loop, each of said segments terminating in a cutting wire second end, said loop being disposed on said first wire guide second end, with said pair of cutting wire segments and said wire second ends extending through said cutter barrel tube and said cutter barrel tube second end and to a position proximal said slot for attachment to said trigger member.

23. An improved biopsy specimen cutter according to claim 1 further comprising:

an elongated rod having first and second ends, said rod movably positioned within said housing and said cutter barrel tube;

a transducer having a sole affixed to said first end of said rod, said transducer including means for generating and receiving ultrasound waves; and a display coupled to said transducer for producing a visual representation according to said ultrasound waves to facilitate positioning said biopsy specimen cutter proximal the tissue sample.

24. An improved biopsy specimen cutter according to claim 23 further comprising a data processing unit coupled between said transducer and said display for converting said sound waves into electronic signals and passing said electronic signals to said display, such that said specimen cutter may be positioned adjacent a target specimen based on said visual representation.

25. An improved biopsy specimen cutter according to claim 23 wherein said sole of said transducer is convex.

26. An improved biopsy specimen cutter according to claim 23 further comprising:

a sheath of flexible material generally surrounding said rod first end and said transducer; and a viscous fluid material interposed between said transducer and said sheath to provide a conducting interface between said transducer and said sheath.

27. A method for excising a tissue sample from a patient with a biopsy specimen cutter that includes an elongated hollow tube having a first end and a second end, a first wire guide having a first end and a second end attached to said cutter barrel tube first end, a cutting wire having a loop formed on a first end of said wire, and at least one wire segment extending from said loop and terminating in a second end of said wire, said loop being disposed said adjacent to second end of said first wire and said wire segment and said wire second end extending longitudinally through said hollow tube and said cutter barrel tube second end, a cutter tip removably attached to said cutter barrel tube first end in enclosing relation to said first wire guide, a trigger housing attached to said cutter barrel tube second end, said housing including a hollow cylinder having an axially extending sidewall with at least one longitudinal slot formed through said sidewall, said wire second end extending through said slot, a trigger mounted within said housing for movement with respect to said housing, said trigger including a member extending through said slot, with said wire second end being attached to said trigger member, said method comprising:

inserting said biopsy specimen cutter into a patient's tissue;

positioning said cutter tip adjacent the tissue sample to be excised;

urging said cutter tip into the tissue such that at least a portion of the tissue sample is positioned within said cutter barrel; and moving said trigger away from said cutter barrel second such that said loop moves across the first wire guide second end, thereby severing the portion of the tissue positioned within said cutter barrel; and excising the tissue sample from the patient such that a void is formed in the patient's tissue.

28. A method according to claim 27 further comprising:

inserting within said specimen cutter a quantity of a radio isotope material of generally corresponding shape and size as the excised tissue sample;

inserting an elongated dilator having first and second ends within said specimen cutter adjacent to said quantity of radio isotope; and urging said particle quantity of radio isotope with said dilator through said specimen cutter into said void.

* * * * *